(12) United States Patent
Green et al.

(10) Patent No.: US 7,772,207 B2
(45) Date of Patent: Aug. 10, 2010

(54) COMBINATION OF A CDK INHIBITOR AND CS-682 OR A METABOLITE THEREOF

(75) Inventors: Simon Richard Green, Dundee (GB); Roger Neil Sleigh, Dundee (GB)

(73) Assignee: Cyclacel Limited, Dundee (GB)

(*) Notice: Subject to any disclaimer, the term of this patent is extended or adjusted under 35 U.S.C. 154(b) by 661 days.

(21) Appl. No.: 10/581,585

(22) PCT Filed: Dec. 3, 2004

(86) PCT No.: PCT/GB2004/005081

§ 371 (c)(1),
(2), (4) Date: Apr. 20, 2007

(87) PCT Pub. No.: WO2005/053699

PCT Pub. Date: Jun. 16, 2005

(65) Prior Publication Data

US 2007/0270442 A1    Nov. 22, 2007

(30) Foreign Application Priority Data

Dec. 4, 2003    (GB) ................. 0328180.5

(51) Int. Cl.
*A61K 31/7064* (2006.01)
*A61K 31/52* (2006.01)
*C07H 19/09* (2006.01)
*C07D 473/16* (2006.01)

(52) U.S. Cl. ............ 514/49; 514/263.4; 536/28.5; 536/28.51; 544/277

(58) Field of Classification Search .............. None
See application file for complete search history.

(56) References Cited

U.S. PATENT DOCUMENTS 5,691,319 A * 11/1997 Kaneko et al. ............. 514/49
6,369,086 B1    4/2002 Davis et al.

FOREIGN PATENT DOCUMENTS

WO    WO-02/46182 A1    6/2002
WO    WO-03/039536 A1    5/2003

OTHER PUBLICATIONS

The Merck Manual of Diagnosis and Therapy, seventeenth edition, 1999, Published by Merck Research Laboratories, pp. 397-398, 948-949, 1916, and 1979-1981.*
The Oxford Textbook of Oncology, 1995, published by Oxford University Press, pp. 447-453.*
Silverman, R., The Organic Chemistry of Drug Design and Drug Action, published 1992 by Academic Press, pp. 4-47.*
"STN Database Descriptions", 2006 Chemical Abstracts Catalog, published 2006 by Chemical Abstracts Service, p. 52.*
Danesi et al., "Pharmacogenetic determinants of anti-cancer drug activity and toxicity" Trends in Pharamcological Sciences (2001) vol. 22 No. 8, pp. 420-426.*
Bibile, K.C. et al, "Cytotoxic synergy between flavopiridol (NSC 649890, L86-8275) and various antineoplastic agents: the importance of sequence of administration," *Cancer Research*, vol. 57(16):3375-3380 (1997).
Hanaoka, Kenji et al, "Antitumor Activity and Novel DNA-Self-Strand-Breaking Mechanism of CNDAC (1-2(2-*C*-Cyano-2-Deoxy-β-D-*Arabino*-Pentofuranosyl) Cytosine) and its $N^4$-Palmitoyl Derivative (CS-682)," *Int. J. Cancer*, vol. 82:226-236 (1999).
STN Gen Caesar accession No. 1364, "Cyclacel's cancer drug starts Phase II testing," Pharma Marketletter Jan. 27, 2002.
Wu, Ming et al, "High-Resolution Magnetic Resonance Imaging of the Efficacy of the Cytosine Analogue 1-[2-*C*-Cyano-2-deoxy-β-D-arabino-pentofuranosyl]-$N^4$-palmitoyl Cytosine (CS-682) in a Liver-Metastasis Athymic Nude Mouse Model," *Cancer Research*, vol. 63:2477-2482 (2003).
Written Opinion of the International Searching Authority for Application No. PCT/GB2004/005081.

* cited by examiner

*Primary Examiner*—Eric S Olson
(74) *Attorney, Agent, or Firm*—Lahive & Cockfield, LLP; Cynthia L. Kanik; Brian C. Trinque

(57) ABSTRACT

A first aspect of the invention relates to a combination comprising a CDK inhibitor and 1-(2-C-cyano-2-dioxy-β-D-arabino-pentofuranosyl)-N4-palmitoyl cytosine, or a metabolite thereof. A second aspect of the invention relates to a pharmaceutical product comprising a CDK inhibitor and 1-(2-C-cyano-2-dioxy-β-D-arabino-pentofuranosyl)-N4-palmitoyl cytosine, or a metabolite thereof, as a combined preparation for simultaneous, sequential or separate use in therapy. A third aspect of the invention relates to a method of treating a proliferative disorder, said method comprising simultaneously, sequentially or separately administering a CDK inhibitor and 1-(2-C-cyano-2-dioxy-β-D-arabino-pentofuranosyl)-N4-palmitoyl cytosine, or a metabolite thereof, to a subject.

5 Claims, No Drawings

US 7,772,207 B2

COMBINATION OF A CDK INHIBITOR AND CS-682 OR A METABOLITE THEREOF

RELATED APPLICATIONS

The present application is a 35 U.S.C. 371 national stage filing of International Application No. PCT/GB2004/005081, filed Dec. 3, 2004; which claims priority to Great Britain Application No. 0328180.5, filed Dec. 4, 2003. The entire contents of each of these applications are hereby incorporated by reference in their entirety.

FIELD OF THE INVENTION

The present invention relates to a pharmaceutical combination suitable for the treatment of cancer and other proliferative disorders.

BACKGROUND TO THE INVENTION

Initiation, progression, and completion of the mammalian cell cycle are regulated by various cyclin-dependent kinase (CDK) complexes, which are critical for cell growth. These complexes comprise at least a catalytic (the CDK itself) and a regulatory (cyclin) subunit. Some of the more important complexes for cell cycle regulation include cyclin A (CDK1—also known as cdc2, and CDK2), cyclin B1-B3 (CDK1), cyclin C (CDK8), cyclin D1-D3 (CDK2, CDK4, CDK5, CDK6), cyclin E (CDK2), cyclins K and T (CDK9) and cyclin H (CDK7). Each of these complexes is involved in a particular phase of the cell cycle.

The activity of CDKs is regulated post-translationally, by transitory associations with other proteins, and by alterations of their intracellular localisation. Tumour development is closely associated with genetic alteration and deregulation of CDKs and their regulators, suggesting that inhibitors of CDKs may be useful anti-cancer therapeutics. Indeed, early results suggest that transformed and normal cells differ in their requirement for e.g. cyclin A/CDK2 and that it may be possible to develop novel antineoplastic agents devoid of the general host toxicity observed with conventional cytotoxic and cytostatic drugs.

The function of CDKs is to phosphorylate and thus activate or deactivate certain proteins, including e.g. retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in e.g. N. Gray, L. Détivaud, C. Doerig, L. Meijer, *Curr. Med. Chem.* 1999, 6, 859) have been found to possess anti-proliferative properties by virtue of CDK-specific ATP antagonism.

Roscovitine is the compound 6-benzylamino-2-[(R)-1-ethyl-2-hydroxyethylamino]-9-isopropylpurine. Roscovitine has been demonstrated to be a potent inhibitor of cyclin dependent kinase enzymes, particularly CDK2. This compound is currently in development as an anti-cancer agent. CDK inhibitors are understood to block passage of cells from the G2/M phase of the cell cycle.

It well established in the art that active pharmaceutical agents can often be given in combination in order to optimise the treatment regime. The present invention therefore seeks to provide a new combination of known pharmaceutical agents that is particularly suitable for the treatment of proliferative disorders, especially cancer. More specifically, the invention centres on the surprising and unexpected effects associated with using certain pharmaceutical agents in combination.

STATEMENT OF INVENTION

In a first aspect, the invention provides a combination comprising a CDK inhibitor and 1-(2-C-cyano-2-dioxy-β-D-arabino-pentofuranosyl)-N4-palmitoyl cytosine, or a metabolite thereof.

A second aspect provides a pharmaceutical composition comprising a combination according to the invention admixed with a pharmaceutically acceptable carrier, diluent or excipient.

A third aspect relates to the use of a combination according to the invention in the preparation of a medicament for treating a proliferative disorder A fourth aspect relates to a pharmaceutical product comprising a CDK inhibitor and 1-(2-C-cyano-2-dioxy-β-D-arabino-pentofuranosyl)-N4-palmitoyl cytosine, or a metabolite thereof, as a combined preparation for simultaneous, sequential or separate use in therapy A fifth aspect relates to a method of treating a proliferative disorder, said method comprising simultaneously, sequentially or separately administering a CDK inhibitor and 1-(2-C-cyano-2-dioxy-β-D-arabino-pentofuranosyl)-N4-palmitoyl cytosine, or a metabolite thereof, to a subject.

A sixth aspect relates to the use of a CDK inhibitor in the preparation of a medicament for the treatment of a proliferative disorder, wherein said treatment comprises simultaneously, sequentially or separately administering a CDK inhibitor and 1-(2-C-cyano-2-dioxy-β-D-arabino-pentofuranosyl)-N4-palmitoyl cytosine, or a metabolite thereof, to a subject.

A seventh aspect relates to the use of a CDK inhibitor and 1-(2-C-cyano-2-dioxy-β-D-arabino-pentofuranosyl)-N4-palmitoyl cytosine, or a metabolite thereof, in the preparation of a medicament for treating a proliferative disorder.

An eighth aspect relates to the use of a CDK inhibitor in the preparation of a medicament for the treatment of a proliferative disorder, wherein said medicament is for use in combination therapy with 1-(2-C-cyano-2-dioxy-β-D-arabino-pentofuranosyl)-N4-palmitoyl cytosine, or a metabolite thereof.

A ninth aspect relates to the use of 1-(2-C-cyano-2-dioxy-β-D-arabino-pentofuranosyl)-N4-palmitoyl cytosine, or a metabolite thereof, in the preparation of a medicament for the treatment of a proliferative disorder, wherein said medicament is for use in combination therapy with a CDK inhibitor.

DETAILED DESCRIPTION

The effect of drug combinations is inherently unpredictable and there is often a propensity for one drug to partially or completely inhibit the effects of the other. The present invention is based on the surprising observation that administering 1-(2-C-cyano-2-dioxy-β-D-arabino-pentofuranosyl)-N4-palmitoyl cytosine and roscovitine in combination, either simultaneously, separately or sequentially, does not lead to any adverse interaction between the two agents. The unexpected absence of any such antagonistic interaction is critical for clinical applications.

In a preferred embodiment, the combination of 1-(2-C-cyano-2-dioxy-β-D-arabino-pentofuranosyl)-N4-palmitoyl cytosine and roscovitine produces an enhanced effect as compared to either drug administered alone. The surprising nature of this observation is in contrast to that expected on the basis of the prior art.

The preferred embodiments as set out below are applicable to all the above-mentioned aspects of the invention.

1-(2-C-cyano-2-dioxy-β-D-arabino-pentofuranosyl)-N⁴-palmitoyl cytosine (I), also known as 2'-cyano-2-deoxy-N⁴-palmitoyl-1-β-D-arabinofuranosylcytosine (Hanaoka, K., et al, *Int. J. Cancer*, 1999:82:226-236; Donehower R, et al, *Proc Am Soc Clin Oncol*, 2000: abstract 764; Burch, P A, et al, *Proc Am Soc Clin Oncol*, 2001: abstract 364), is an orally administered novel 2'-deoxycytidine antimetabolite prodrug of the nucleoside CNDAC, 1-(2-C-Cyano-2-deoxy-β-D-arabino-pentafuranosyl)-cytosine.

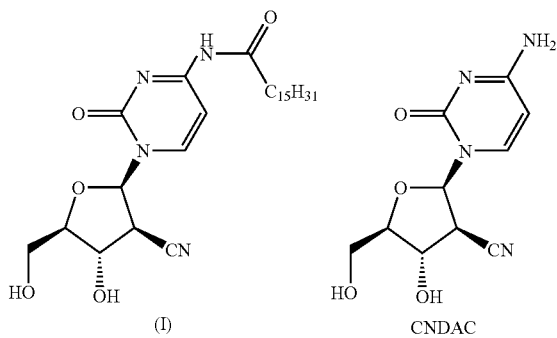

1-(2-C-cyano-2-dioxy-β-D-arabino-pentofuranosyl)-N⁴-palmitoyl cytosine (I) has a unique mode of action over other nucleoside metabolites such as gemcitabine in that it has a spontaneous DNA strand breaking action, resulting in potent anti-tumour activity in a variety of cell lines, xenograft and metastatic cancer model.

1-(2-C-cyano-2-dioxy-β-D-arabino-pentofuranosyl)-N⁴-palmitoyl cytosine (I) has been the focus of a number of studies in view of its oral bioavailability and its improved activity over gemcitabine (the leading marketed nucleoside analogue) and 5-FU (a widely-used antimetabolite drug) based on preclinical data in solid tumours. Recently, investigators reported that (I) exhibited strong anticancer activity in a model of colon cancer. In the same model, (I) was found to be superior to either gemcitabine or 5-FU in terms of increasing survival and also preventing the spread of colon cancer metastases to the liver (Wu M, et al, *Cancer Research*, 2003: 63:2477-2482). To date, phase I data from patients with a variety of cancers suggest that (I) is well tolerated in humans, with myelosuppression as the dose limiting toxicity.

Preferably the CDK inhibitor is an inhibitor of CDK2 and/or CDK4. More preferably the CDK inhibitor is selected from roscovitine, purvalanol A, purvalanol B, olomucine and other 2,6,9-trisubstituted purines as described in WO97/20842, WO98/05335 (CV Therapeutics), WO99/07705 (Regents of the University of California). Even more preferably the CDK inhibitor is selected from roscovitine and purvalanol A. More preferably still, the CDK inhibitor is roscovitine.

The term "proliferative disorder" is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, anti-parasitic disorders such as malaria, emphysema and alopecia. In these disorders, the compounds of the present invention may induce apoptosis or maintain stasis within the desired cells as required. Preferably, the proliferative disorder is a cancer or leukaemia, most preferably cancer of the lung, prostate, bladder, head and neck, colon, sarcoma or lymphoma.

In a particularly preferred embodiment, the invention relates to the use of the combination described hereinbefore in the treatment of a CDK dependent or sensitive disorder. CDK dependent disorders are associated with an above normal level of activity of one or more CDK enzymes. Such disorders are preferably associated with an abnormal level of activity of CDK2 and/or CDK4. A CDK sensitive disorder is a disorder in which an aberration in the CDK level is not the primary cause, but is downstream of the primary metabolic aberration. In such scenarios, CDK2 and/or CDK4 can be said to be part of the sensitive metabolic pathway and CDK inhibitors may therefore be active in treating such disorders. Such disorders are preferably cancer or leukaemic disorders.

As used herein the phrase "preparation of a medicament" includes the use of the components of the invention directly as the medicament in addition to their use in any stage of the preparation of such a medicament.

In one preferred embodiment of the invention, the CDK inhibitor is administered sequentially or separately prior to the 1-(2-C-cyano-2-dioxy-β-D-arabino-pentofuranosyl)-N4-palmitoyl cytosine. Preferably, the CDK inhibitor is administered at least 4 hours before the 1-(2-C-cyano-2-dioxy-β-D-arabino-pentofuranosyl)-N4-palmitoyl cytosine, and more preferably at least 72 hours before the 1-(2-C-cyano-2-dioxy-β-D-arabino-pentofuranosyl)-N4-palmitoyl cytosine.

In a particularly preferred embodiment, the 1-(2-C-cyano-2-dioxy-β-D-arabino-pentofuranosyl)-N4-palmitoyl cytosine is administered sequentially or separately prior to the CDK inhibitor. Preferably, the 1-(2-C-cyano-2-dioxy-β-D-arabino-pentofuranosyl)-N4-palmitoyl cytosine is administered at least one hour before the CDK inhibitor, and more preferably at least 24 hours before the CDK inhibitor.

In one preferred embodiment, the CDK inhibitor and 1-(2-C-cyano-2-dioxy-β-D-arabino-pentofuranosyl)-N4-palmitoyl cytosine are each administered in a therapeutically effective amount with respect to the individual components; in other words, the CDK inhibitor and 1-(2-C-cyano-2-dioxy-β-D-arabino-pentofuranosyl)-N4-palmitoyl cytosine are administered in amounts that would be therapeutically effective even if the components were administered other than in combination.

In another preferred embodiment, the CDK inhibitor and 1-(2-C-cyano-2-dioxy-β-D-arabino-pentofuranosyl)-N4-palmitoyl cytosine are each administered in a sub-therapeutic amount with respect to the individual components; in other words, the CDK inhibitor and 1-(2-C-cyano-2-dioxy-β-D-arabino-pentofuranosyl)-N4-palmitoyl cytosine are administered in amounts that would be therapeutically ineffective if the components were administered other than in combination.

Preferably, the 1-(2-C-cyano-2-dioxy-β-D-arabino-pentofuranosyl)-N4-pahnitoyl cytosine and CDK inhibitor interact in a synergistic manner. As used herein, the term "synergistic" means that 1-(2-C-cyano-2-dioxy-β-D-arabino-pentofuranosyl)-N4-palmitoyl cytosine and the CDK inhibitor produce a greater effect when used in combination than would be expected from adding the individual effects of the two components. Advantageously, a synergistic interaction may allow for lower doses of each component to be administered to a patient, thereby decreasing the toxicity of chemotherapy, whilst producing and/or maintaining the same therapeutic effect. Thus, in a particularly preferred embodiment, each component can be administered in a sub-therapeutic amount.

Metabolite

As used herein, the term "metabolite" encompasses chemically modified entities that are produced by metabolism of 1-(2-C-cyano-2-dioxy-β-D-arabino-pentofuranosyl)-N4-palmitoyl cytosine.

In one particularly preferred embodiment of the invention, the metabolite of 1-(2-C-cyano-2-dioxy-β-D-arabino-pentofuranosyl)-N4-palmitoyl cytosine is 2'-C'-cyano-2'-dioxy-1-β-D-arabino-pentofuranosyl cytosine (CNDAC).

In another particularly preferred embodiment of the invention, 1-(2-C-cyano-2-dioxy-β-D-arabino-pentofuranosyl)-N4-palmitoyl cytosine is metabolized intracellularly to the active metabolite CNDAC-triphosphate (CNDACTP), a process involving both the cleavage of the palmitoyl moiety and activation to CNDACTP by the action of nucleoside kinases.

Salts/Esters

The agents of the present invention can be present as salts or esters, in particular pharmaceutically acceptable salts or esters.

Pharmaceutically acceptable salts of the agents of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

The invention also includes where appropriate all enantiomers and tautomers of the agents. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the agents of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or pharmaceutically acceptable salts thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the agents of the present invention. The terms used in the claims encompass these forms.

Polymorphs

The invention furthermore relates to agents of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes agents of the present invention in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 2000 mg and more preferably from 50-1000 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-500 mg, of active ingredient per dose.

Compositions may be formulated in unit dosage form, i.e., in the form of discrete portions containing a unit dose, or a multiple or sub-unit of a unit dose.

In a particularly preferred embodiment, the combination or pharmaceutical composition of the invention is administered intravenously.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.1 to 30 mg/kg body weight, such as from 2 to 20 mg/kg, more preferably from 0.1 to 1 mg/kg body weight.

By way of guidance, 1-(2-C-cyano-2-dioxy-β-D-arabino-pentofuranosyl)-N4-palmitoyl cytosine is typically administered in accordance to a physicians direction at dosages between 1 and 120 mg/m² body surface orally. The doses can be given 5 days a week for 4 weeks, or 3 days a week for 4 weeks. Dosages and frequency of application are typically adapted to the general medical condition of the patient and to the severity of the adverse effects caused, in particular to those caused to the hematopoietic, hepatic and to the renal system.

Roscovitine is typically administered from about 0.05 to about 5 g/day, preferably from about 0.4 to about 3 g/day. Roscovitine is preferably administered orally in tablets or capsules. The total daily dose of roscovitine can be administered as a single dose or divided into separate dosages administered two, three or four time a day.

Preferably, roscovitine is administered as an orally or intravenously at a dosage of from 0.4 to 3 g/day. 1-(2-C-cyano-2-dioxy-β-D-arabino-pentofuranosyl)-N4-palmitoyl cytosine is then administered in the manner deemed most suitable at an appropriate dosage as discussed above. Preferably, the 1-(2-C-cyano-2-dioxy-β-D-arabino-pentofuranosyl)-N4-pahnitoyl cytosine is administered at least 24 hours after the administration of roscovitine.

The present invention is further described by way of example.

EXAMPLES

The growth inhibitory activity of roscovitine was measured alone and in combination with 1-(2-C-cyano-2-dioxy-β-D-arabino-pentofuranosyl)-N4-palmitoyl cytosine against a variety of cell lines using a monolayer assay and a tumour stem cell assay.

Methods and Materials

Compound

Stock solutions of CDK inhibitor (for example roscovitine) were prepared in DMSO and aliquots stored at −20° C. Final dilutions were prepared in culture medium (Iscove's Modified Dulbecco's Medium; Life Technologies, Karlsruhe) immediately prior to use.

Clonogenic Assay

Preparation of Single Cell Suspensions from Human Tumor Xenografts

Solid human tumor xenografts growing subcutaneously in serial passages in thymus aplastic nude mice (NMRI, Naval Medical Research Institute, USA, nu/nu strain, obtained from our own breeding facility) were removed under sterile conditions, mechanically disaggregated and subsequently incubated with an enzyme cocktail consisting of collagenase (41 U/ml, Sigma), DNAse I (125 U/ml, Roche), hyaluronidase (100 U/ml, Sigma) and dispase II (1.0 U/ml, Roche) in RPMI 1640-Medium (Life Technologies) at 37° C. for 30 minutes. Cells were passed through sieves of 200 μm and 50 μm mesh size and washed twice with sterile PBS-buffer (Life Technologies). The percentage of viable cells was determined in a Neubauer-hemocytometer using trypan blue exclusion.

Culture Methods

The clonogenic assay was performed in a 24-well format according to a modified two-layer soft agar assay introduced by Hamburger & Salmon [Alley, M. C., Uhi, C. B. & M. M. Lieber, 1982]. Improved detection of drug cytotoxicity in the soft agar colony formation assay through use of a metabolizable tetrazolium salt. *Life Sci*. 31: 3071-3078]. The bottom layer consisted of 0.2 ml/well of Iscove's Modified Dulbecco's Medium (supplemented with 20% (v/v) fetal calf serum and 0.01% (v/v) gentamicin) and 0.75% (w/v) agar. $4 \cdot 10^4$ to $8 \cdot 10^4$ cells were added to 0.2 ml of the same culture medium supplemented with 0.4% (w/v) agar and plated in 24-multiwell dishes onto the bottom layer. Cytostatic drugs were applied by continuous exposure (drug overlay) in 0.2 ml culture medium. Every dish included six control wells containing the vehicle and drug treated groups in triplicate at 6 concentrations. Cultures were incubated at 37° C. and 7.5% $CO_2$ in a humidified atmosphere for 8-20 days and monitored closely for colony growth using an inverted microscope. Within this period, in vitro tumor growth led to the formation of colonies with a diameter of >50 μm. At the time of maximum colony formation, counts were performed with an automatic image analysis system (OMNICON FAS IV, Biosys GmbH). 24 hours prior to evaluation, vital colonies were stained with a sterile aqueous solution of 2-(4-iodophenyl)-3-(4-nitrophenyl)-5-phenyltetrazolium chloride (1 mg/ml, 100 μl/well) [i].

An assay was considered fully evaluable, if the following quality control criteria were fulfilled:

Mean number of colonies in the control group wells of 24-multiwell plates ≧20 colonies with a colony diameter of >50 μm The positive reference compound 5-fluorouracil (5_FU) (at the toxic dose of 1000 μg/ml) must effect a colony survival of <20% of the controls Initial plate counts on day 0 or 2<20% of the final control group count Coefficient of variation in the control group ≦50%

Data Evaluation

Drug effects were expressed in terms of the percentage of survival, obtained by comparison of the mean number of colonies in the treated plates with the mean colony count of the untreated controls (relative colony count expressed by the test-versus-control-group value, T/C-value [%]):

$$\frac{T}{C} = \frac{\text{colony } count_{treated\ group}}{\text{colony } count_{control\ group}} \cdot 100\ [\%].$$

IC50- and IC70-values, being the drug concentration necessary to inhibit colony formation by 50% (T/C=50%) and 70% (T/C=30%) respectively, were determined by plotting compound concentration versus relative colony count. Mean IC50- and IC70-values were calculated according to the formula $$\text{mean } IC_{50,70} = 10^{\left(\frac{\sum_{x=1}^{n} lg(IC_{50,70})}{n}\right)}$$

with x the specific tumor model, and n the total number of tumor models studied. If an IC50- or IC70-value could not be determined within the examined dose range, the lowest or highest concentration studied was used for the calculation.

In the mean graph analysis (IC-plot) the distribution of IC70-values obtained for a test compound in the individual tumor types is given in relation to the mean IC70-value, obtained for all tumors tested. The individual IC70-values are expressed as bars in a logarithmically scaled axis. Bars to the left demonstrate IC70-values lower than the mean value (indicating more sensitive tumor models), bars to the right demonstrate higher values (indicating rather resistant tumor models). The IC-plot therefore represents a fingerprint of the antiproliferative profile of a compound.

Test procedure: Combination of Roscovitine with Standard Agents Cell Lines

The characteristics of the 6 human tumor cell lines are shown in Table 1.

TABLE 1

Cell Lines used for Testing Roscovitine in Combination with standard agents

| Tumor Type Formation | Cell Line | Histology in nude mice | Doubling Time [h] | Tumor in vivo |
|---|---|---|---|---|
| Colon | DLD1 | adeno ca | nd | yes |
|  | HT29 | pd adeno ca | 23 | yes |
| Lung, NSC | LXFA 629L | adeno carcinoma | 31 | yes |
| Prostate | 22RV1 | nd | 40 | yes |
|  | DU145 | adeno ca | nd | yes |
|  | PC3M | pd adeno ca | nd | yes | ud = undifferentiated,
pd = poorly differentiated,
md = moderately differentiated,
wd = well differentiated,
mm = malignant melanoma;
ND = not determined The lung carcinoma cell line LXFA 629L was established from a human tumor xenograft as described by Roth et al. 1999 [Roth T, Burger A M, Dengler W, Willmann H, Fiebig H H. Human tumor cell lines demonstrating the characteristics of patient tumors as useful models for anticancer drug screening. In: Fiebig H H, Burger A M (eds). Relevance of Tumor Models for Anticancer Drug Development. *Contrib. Oncol.* 1999, 54: 145-156]. The origin of the donor xenograft was described by Fiebig et al. 1992 [Fiebig H H, Dengler W A, Roth T. Human tumor xenografts: Predictivity, characterization, and discovery of new anticancer agents. In: Fiebig H H, Burger A M (eds). Relevance of Tumor Models for Anticancer Drug Development. *Contrib. Oncol.* 1999, 54: 29-50].

The cell lines DLD1 and HT29 (colon), as well as the prostate carcinoma DU145 and PC3M were obtained from US-NCI (National Cancer Institute, USA).

The prostate carcinoma 22RV1 was purchased from the American Type Culture Collection (ATCC).

Cells were routinely passaged once or twice weekly. They were maintained no longer than 20 passages in culture. All cells were grown at 37° C. in a humidified atmosphere (95% air, 5% $CO_2$) in RPMI 1640 medium (Invitrogen, Karlsruhe, Germany) supplemented with 10% fetal calf serum (Sigma, Deisenhofen, Germany) and 0.1% gentamicin (Invitrogen).

Cell Proliferation Assay

A modified propidium iodide assay was used to assess the effects of roscovitine on the growth of the human tumor cell lines [Dengler W A, Schulte J, Berger D P et al. (1995). Development of a propidium iodide fluorescence assay for proliferation and cytotoxicity assay. *Anti-Cancer Drugs* 1995, 6:522-532]. Briefly, cells are harvested from exponential phase cultures by trypsination, counted and plated in 96 well flat-bottomed microtiter plates at a cell density dependent on the cell line (5-12.000 viable cells/well). After 24 h recovery to allow the cells to resume exponential growth, 20 μl of culture medium (3 control wells per plate) or culture medium containing various concentrations of test article no. 1 (standard agent) was added to the wells. Each concentration was plated in triplicate. On each plate test article no. 1 is applied in five concentrations 4 times in 4 quarters of the microtiter plate. Quarter 1 was for the test article no. 1 alone, in quarters 2-4 the test article no. 2 (roscovitine) was applied at three different time points, respectively. Following 4 days of continuous test article exposure, cell culture medium with or without drug was replaced by 200 μl of an aqueous propidium iodide (PI) solution (7 μg/ml). Since PI only passes through leaky or lysed cell membranes, DNA of dead cells could be stained and measured, while living cells were not be stained. To measure the proportion of living cells, cells were permeabilized by freezing the plates, resulting in death of all cells. After thawing of the plates fluorescence was then measured using the Cytofluor 4000 microplate reader (excitation 530 nm, emission 620 nm), giving a direct relationship to the total cell number. Growth inhibition was expressed as treated/control×100 (% T/C) and $IC_{50}$, $IC_{70}$ and $IC_{90}$ values for each combination were determined by plotting compound concentration versus cell viability.

MTT Assay

The system which was utilized for the evaluation of roscovitine with and without 1-(2-C-cyano-2-dioxy-β-D-arabino-pentofuranosyl)-N4-palmitoyl cytosine with the MTT assay. The MTT assay is a spectrophotometric assay based on the ability of viable cells to convert MTT to formazan. Cell concentrations were estimated by measuring absorbance at test wavelength of 570 nm and a reference wavelength of 630 nm. An automated procedure was utilized to determine the $IC_{50}$ value (concentration of drug which inhibits cell growth by 50% of the control) of all agents used in these studies. Cell lines were selected with specific possibilities in mind for future clinical trial designs.

Initially, roscovitine and 1-(2-C-cyano-2-dioxy-β-D-arabino-pentofuranosyl)-N4-palmitoyl cytosine were tested separately over a range of concentrations. After the initial $IC_{50}$ analysis was complete, the combinations were then tested. For the combination studies, the concentration (expressed as a percent of the individual agent's $IC_{50}$) schema used to characterise the type of interaction is shown below:

| Drug Concentration (Expressed as a percent of the $IC_{50}$) ||
| --- | --- |
| Roscovitine | 1-(2-C-cyano-2-dioxy-β-D-arabino-pentofuranosyl)-N4-palmitoyl cytosine (I) |
| 100 | 0 |
| 75 | 25 |
| 60 | 40 |
| 50 | 50 |
| 40 | 60 |
| 25 | 75 |
| 0 | 100 |
| 0 | 0 |

Statistical Analysis of Combination Studies

To interpret the combination curves, statistical comparisons were made with each test combination (75:25 roscovitine/1-(2-C-cyano-2-dioxy-β-D-arabino-pentofuranosyl)-N4-palmitoyl cytosine) and the endpoints (100:0-roscovitine and 0:100-1-(2-C-cyano-2-dioxy-β-D-arabino-pentofuranosyl)-N4-palmitoyl cytosine). A statistically significant observation requires that a difference exists between the combination (roscovitine and 1-(2-C-cyano-2-dioxy-β-D-arabino-pentofuranosyl)-N4-palmitoyl cytosine) absorbance value and both endpoint values (roscovitine and 1-(2-C-cyano-2-dioxy-β-D-arabino-pentofuranosyl)-N4-palmitoyl cytosine alone) [Greco et al, The search for synergy; A critical review from a response surface perspective. Pharmacol; Review 47:331-385, 1995; Laska et al, Simple designs and model-free tests for synergy; Biometrics 50:834-841, 1994]. If the majority of ($\geq$3 of 5) of the values are statistically above or below the line (endpoints) then antagonism or synergy is described, respectively. Otherwise, the pattern is more consistent with an additive interaction.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The invention claimed is:

1. A method of treating a proliferative disorder, wherein the proliferative disorder is selected from lung cancer, prostate cancer, bladder cancer, head and neck cancer, colon cancer, sarcoma and lymphoma, said method comprising sequentially administering to a subject 1-(2-C-cyano-2-deoxy-β-D-arabino-pentofuranosyl)-N4-palmitoyl cytosine, or metabolite thereof, wherein the metabolite is 1-(2-C-Cyano-2-deoxy-β-D-arabino-pentafuranosvl)-cytosine, and roscovitine.

2. A method according to claim 1 which comprises administering roscovitine, to a subject prior to sequentially administering 1-(2-C-cyano-2-deoxy-β-D-arabino-pentofuranosyl)-N4-palmitoyl cytosine, or metabolite thereof, to said subject.

3. A method according to claim 1 which comprises administering 1-(2-C-cyano-2-deoxy-β-D-arabino-pentofuranosyl)-N4-palmitoyl cytosine, or metabolite thereof, to a subject prior to sequentially administering roscovitine to said subject.

4. A method according to claim 1 wherein the roscovitine and 1-(2-C-cyano-2-deoxy-β-D-arabino-pentofuranosyl)-N4-palmitoyl cytosine, or metabolite thereof, are each administered in a therapeutically effective amount with respect to the individual components.

5. A method according to claims 1 wherein the roscovitine and 1-(2-C-cyano-2-deoxy-β-D-arabino-pentofuranosyl)-N4-palmitoyl cytosine, or metabolite thereof, are each administered in a subtherapeutic amount with respect to the individual components.

* * * * *